United States Patent [19]
Cominelli et al.

[11] Patent Number: 5,942,390
[45] Date of Patent: Aug. 24, 1999

[54] METHOD OF DIAGNOSING PREDISPOSITION FOR ULCERATIVE COLITIS IN JEWISH POPULATION BY DETECTION OF INTERLEUKIN-1 RECEPTOR ANTAGONIST POLYMORPHISM

[75] Inventors: Fabio Cominelli; Theresa Pizarro, both of Charlottesville, Va.; Jerome I. Rotter, Los Angeles; Huiying Yang, Cerritos, both of Calif.

[73] Assignee: Cedars-Sinai Medical Center, Los Angeles, Calif.

[21] Appl. No.: 08/587,911

[22] Filed: Jan. 12, 1996

[51] Int. Cl.$^6$ .............................. C12Q 1/68; C12P 21/06; C07K 1/00; C07H 21/04
[52] U.S. Cl. ........................... 435/6; 435/69.1; 435/91.1; 435/172.3; 435/333; 530/350; 935/18; 935/78; 536/24.33; 536/23.1
[58] Field of Search .................................. 435/69.1, 91.1, 435/172.3, 335; 530/350; 935/18, 78; 536/24.33, 23.1

[56] References Cited

PUBLICATIONS

Roth, M-P, et al., "Familial Empiric Risk Estimates of Inflammatory Bowel Disease in Ashkenazi Jews", *Gastroenterology*, 96:1016–1020, 1989.

Bioque, G., et al., "Further Evidence For a Genetic Association of Interleukin–1 Receptor Antagonist With Ulcerative Colitis In A Northern And A Mediterranean Population," *Gastroenterology*, 108(4):a783 (Apr. 1995).

Duerr, R.H., et al., "Association Between Ulcerative Colitis And A Polymorphism In Intron 2 Of The Interleukin–1 Receptor Antagonist Gene," *Gastroenterology*, 108(4):a812 (Apr. 1995).

Mansfield, J., et al., "Novel Genetic Association Between Ulcerative Colitis And The Anti–inflammatory Cytokine Interleukin–1 Receptor Antagonist," *Gastroenterology*, 106(3):637–642 (Mar. 1994).

Tountas, N.A., et al., "Genetic Association Between Allele 2 of IL–1 Receptor Antagonist (IL–1ra) And Ulcerative Colitis (UC) in a Los Angeles Based Hispanic Population," *Gastroenterology*, 108(4):a930 (Apr. 1995).

Tountas, N.A. et al., Hetrogenous Association Between Allele 2 of IL–1 Receptor Antagonist (IL–1ra) And Ulcerative Colitis (UC) In Jewish And Non–Jewish Populations *J. Investigative Medicine*, 44(1):a175 (Jan. 1996).

Casini–Raggi, V., et al., "Mucosal Imbalance of IL–1 and IL–1 Receptor Antagonist in Inflammatory Bowel Disease; A Novel Mechanism of Chronic Intestinal Inflammation." *J. Immunol.*, :2434–2440 (1995).

Mansfield, J.C., et al., "Novel Genetic Association Between Ulcerative Colitis and the Anti–inflammatory Cytokine Interleukin–1 Receptor Antagonist." *Gastroenterology*, 106:637–642 (1994).

Tarlow, J.K., et al., "Polymorphism in Hhuman IL–1 Receptor Antagonist Gene Intron 2 is Caused by Variable Numbers of an 86–bp Tandem Repeat." *Hum. Genet.*, 91:403–404 (1993).

*Primary Examiner*—Jeffrey Stucker
*Assistant Examiner*—Hankyel T. Park
*Attorney, Agent, or Firm*—Pretty, Schroeder & Poplawski

[57] ABSTRACT

A novel, differential association between allele 2 of the variable number of tandem repeats polymorphism at intron 2 of the human IL-1 receptor antagonist gene and ulcerative colitis in humans of Jewish ancestry has been discovered. In accordance with the present invention, there is provided methods of screening for ulcerative colitis in human subjects of Jewish ancestry comprising detecting the presence or absence of nucleic acid of the subject encoding allele 2 of the variable number of tandem repeats polymorphism at intron 2 of the human IL-1 receptor antagonist gene, wherein the presence of nucleic acid encoding allele 2 is indicative of ulcerative colitis. Kits useful for screening for ulcerative colitis in human subjects of Jewish ancestry are also provided.

31 Claims, No Drawings

METHOD OF DIAGNOSING PREDISPOSITION FOR ULCERATIVE COLITIS IN JEWISH POPULATION BY DETECTION OF INTERLEUKIN-1 RECEPTOR ANTAGONIST POLYMORPHISM

BACKGROUND OF THE INVENTION

A. Inflammatory Bowel Disease

Inflammatory bowel disease (IBD) is the collective term used to describe two chronic, idiopathic gastrointestinal disorders: ulcerative colitis ("UC") and Crohn's disease ("CD"). Although the diseases have distinct pathophysiological characteristics, they are frequently considered together due to several clinical and therapeutic similarities. Several other types of inflammatory conditions of the bowel having known infectious, toxic or ischemic etiology, such as irritable bowel syndrome, infectious diarrhea, rectal bleeding, radiation colitis, and the like, may mimic IBD acutely, because the mucosa of the small and large intestines reacts in a similar way to a large number of different insults. However, if the disease progression is monitored over time, they can be distinguished from IBD by their failure to cause a chronic relapsing and remitting syndrome.

IBD occurs world-wide and is reported to afflict as many as two million people. The course and prognosis of IBD is widely variable. Onset has been documented at all ages; however, IBD predominately begins in young adulthood. The three most common presenting symptoms of IBD are diarrhea, abdominal pain, and fever. The diarrhea may range from mild to severe and is often accompanied by urgency and frequency. In UC, the diarrhea is usually bloody and may contain mucus and purulent matter as well. Anemia and weight loss are additional common signs of IBD. Ten to fifteen percent of all patients with IBD will require surgery over a 10-year period. The risk for the development of cancer is increased in patients with IBD as well, particularly in those with UC. The longer the duration of disease, the higher the risk of developing carcinoma. Patients with UC regularly undergo cancer surveillance by endoscopy after ten years of disease. Reports of an increasing occurrence of psychological problems, including anxiety and depression, are perhaps not surprising secondary effects of what is often a debilitating disease that occurs in people in the prime of life.

B. The Cause(s) of IBD are Unknown

Although the etiology of IBD is unknown, a number of studies have suggested that genetics is important in a person's susceptibility to IBD and that the immune system is responsible for mediating the tissue damage in these diseases. Generally speaking, a failure to down regulate the normal self-limited inflammatory response of the bowel is characteristic of IBD, but it remains unclear what initiates the pathogenic processes and how it may differ, if at all, in UC and CD.

It has also been suggested that a primary abnormality of the immune system and its regulation might serve as primary initiating factors, or that the disease process might be initiated by an infectious agent and the injury is then perpetuated through immune-mediated or other processes. Although the mucosal injury observed during episodes of acute disease can resemble the effects of any of a number of recognized infectious agent, no transmissible infectious agent has been consistently identified with IBD.

Autoimmunity has also been suggested in the pathogenesis of IBD. Evidence to suggest this hypothesis is based on the existence of circulating antibodies that react with unknown alimentary tract antigens of both human and animal origin. For example, human fetal and adult colonic, biliary, skin and vascular epithelial cells, epithelial cell associated components from murine small intestine, rat and human colonic epithelial glycoproteins, intestinal bacterial polysaccharide, and antigens from germ-free rat feces have been described to react with sera from patients with IBD. Other studies demonstrated an increased local IgG response in the colonic mucosa of patients with IBD and other colonic inflammations. The mechanism of this IgG response, the specific local antigens involved, and the role of these antibodies are unknown.

C. Need for Objective Diagnostic Tools

Inflammatory bowel disease poses a clinical and scientific challenge to physicians and researchers. To date most of the diagnostic tools for IBD are quite subjective. Diagnosis depends upon a host of procedures aimed at confirming the suspected diagnosis. The initial symptoms are often confused for non-chronic bowel disorders by physicians unfamiliar with IBD, because the mucosa of the small and large intestines reacts in a similar way to a large number of different insults. Consequently, IBD often goes mistreated and undiagnosed until the disease shows its chronicity which results in referral of the patient to a specialist. The imprecise and subjective nature of endoscopic and radiologic examination can result in a misdiagnosis or indeterminate diagnosis even when the IBD is suspected. Unfortunately, the patient must often suffer as the disease progresses before a definitive diagnosis can be made. In many patients, though, the diagnosis of IBD must still be regarded as indeterminate.

The differentiation between the types of IBD, ulcerative colitis and Crohn's disease, carries important prognostic and therapeutic implications. For example, when colectomy is indicated, the type of IBD involved determines which surgical options are appropriate. Surgery (total colectomy) does represent a cure for the symptoms of UC, though a dramatic one. In CD, surgery is never curative. Continent procedures such as the ileorectal pull-through (mucosal proctectomy) or the Kock pouch may be desirable in UC, but are contraindicated in CD.

Thus, IBD and quite often its treatment affects the lifestyle and functional capabilities of those afflicted. Treatment courses often result in adverse physiologic manifestations which must be balanced against the therapeutic benefit. Any intervention which can improve patients' toleration of their disease and therapeutic program is welcome.

The availability of diagnostic methods that would readily distinguish UC from CD as well as other inflammatory disorders of the bowel would represent a major clinical advance which would aid in therapeutic management of IBD and the design of more specific treatment modalities. In addition specific detection of the disease in prospective parents can be useful in genetic counseling. Accordingly, there has existed a need for convenient and reliable methods of screening for IBD for diagnostic, prognostic and therapeutic purposes.

BRIEF DESCRIPTION OF THE INVENTION

A powerful association has been discovered in Jews between ulcerative colitis ("UC") and the presence of allele 2 of the variable number of tandem repeats ("VNTR") polymorphism at intron 2 of the human interleukin-1 receptor antagonist ("IL-1ra") gene. This association provides the basis for convenient and reliable methods of screening Jewish patients for UC, and distinguishing UC from Crohn's disease ("CD") and other inflammatory diseases of the bowel.

The present invention provides novel methods of screening for UC in Jews which comprise detecting the presence or absence of nucleic acid encoding allele 2 of the VNTR polymorphism at intron 2 of the IL-1ra gene, wherein the presence of nucleic acid encoding allele 2 indicates UC. These novel methods do not depend upon the presentation of clinical symptoms or the activity of the disease and provide a more sensitive method of screening for UC within this sub-population than is provided by prior art methods. Thus, the present invention has both prognostic and diagnostic value.

Nucleic acid encoding allele 2 of VNTR polymorphism of the IL-1ra gene can be detected in accordance with the present invention by amplifying the genomic DNA of a Jewish subject which encodes at least the portion intron 2 of the IL- 1ra gene encoding the VNTR allele and identifying the allele present. Allele 2 can be identified by assaying the nucleic acid sequence at intron 2 of the IL-1ra gene of a subject for defining characteristics of allele 2 and comparing the results to a positive and or negative control. Defining characteristics of nucleic acid encoding allele 2 include, for example, size, sequence, homology to a probe, and the like. Thus there are an array of different formats in which the methods of the present invention can be performed. Primers suitable for use in amplifying nucleic acid encoding intron 2 of the IL-1ra gene are provided herein.

Also provided by the present invention are kits for screening for UC in Jews by detecting the presence or absence of allele 2 of the VNTR polymorphism at intron 2 of the IL-1ra gene. Such kits include reagents, primers, sequencing markers, positive and negative controls and the like, which are useful in the practice of the present invention.

DETAILED DESCRIPTION OF THE INVENTION

Although the clinical features of ulcerative colitis ("UC") and Crohn's disease ("CD") have been well characterized, diagnosis of these disease is often a protracted and expensive undertaking that requires invasive and unpleasant procedures. The etiology and pathogenesis of these chronic, relapsing inflammatory bowel diseases ("IBD") remain unknown. Several factors have been implicated as possible initiating events in IBD, including environmental agents, bacterial or viral organisms, bacterial cell wall components or ingested toxins, and dietary products. These factors, capable of initiating an inflammatory response in genetically predisposed individuals, may initiate a sequence of chronic immunological processes that are not appropriately downregulated. These events perpetuate a prolonged cellular and humoral immune response that leads to subsequent tissue injury.

The search for a specific genetic marker which would provide a non-invasive, convenient and reliable method of diagnosing IBD has been frustrated by the apparent heterogeneity of these diseases. Certainly, there can be no group more troubled by this than people of Jewish ancestry, particularly Caucasians of Jewish ancestry, who as a group, show the highest reported risk of developing IBD than any other ethnic group. While UC and CD are both found worldwide, they occur in the highest frequency in North America and Northern Europe where the incidence ranges from 2 to 15 and the prevalence 35–150 per 1000,000 for UC, and 2–7 and 30–100 per 100,000 for CD, respectively. The incidence of IBD is highest among Caucasians, lower in blacks, and lowest in Asians. For Caucasians, the most consistent observation has been that Ashkenazi Jewish populations has been shown to be at a higher risk of developing IBD than other ethnic groups.

A differential association between UC and the presence of allele 2 of the variable number tandem repeat polymorphism at intron 2 of the interleukin-1 receptor antagonist gene in human subjects of Jewish ancestry has been discovered. This association provides the basis for convenient and reliable methods of screening for UC in human subjects of Jewish ancestry, providing valuable information in the diagnosis of IBD and the determination of susceptibility to UC.

Interleukin-1 ("IL-1") is a pro-inflammatory cytokine produced predominately by activated macrophages. IL-1 induces fever, release of acute phase reactants, production of arachidonic acid metabolites, and activation of other immune cells.

The cytokine interleukin-1 receptor antagonist ("IL-1ra ") is a potent anti-inflammatory protein that appears to play a role in several chronic inflammatory bowel diseases including IBD. The inflammatory response to IL-1 is modulated by IL-1ra, a 22 kilodalton protein secreted by the same cells that produce IL-1. The IL-1ra is structurally related to IL-1$\alpha$ and IL-1$\beta$ and competes with these molecules for occupancy of IL-1 cell surface receptors. Since IL-1ra does not trigger signal transduction, it acts as a competitive inhibitor. It may therefore play a crucial role in many IL-1 mediated diseases, acting as an important endogenous regulator of inflammation.

The gene encoding IL-1ra is located on human chromosome 2 (2q13–14). The published gene sequence of IL-1ra shows four copies of an 86-base pair sequence in intron 2 of the IL-1ra gene. See, Lennard, A. et al., Cytokine 4:83–89 (1992), incorporated herein by reference in its entirety. Recently, a variable length polymorphism was reported at intron 2 of the IL-1ra gene, comprising five alleles. See, Tarlow, J., et. al., Human Genetics 91:403–404 (1993), incorporated herein by reference in its entirety. This polymorphism is referred to herein as the variable number of tandem repeats ("VNTR") polymorphism of the IL-1ra gene.

Alleles 1 through 5 (A1–A5) of the VNTR polymorphism are characterized by the number of copies of the 86-base pair sequence present at the loci as described in Table 1. These alleles can be easily distinguished from one another on the basis of their unique lengths, by direct sequencing and the like. For example, primers flanking this region of the VNTR polymorphism can be used to amplify the polymorphic region by PCR. The PCR products can then be analyzed by electrophoresis to determine the allele present. The primers defined as SEQ ID NO 1 and SEQ ID NO 2 have been used to amplify genomic DNA encoding the VNTR polymorphism of IL-1ra and the five alleles characterized as follows in Table 1:

TABLE 1

Five alleles identified from DNA amplified from 70 unrelated individuals Tarlow, J., et. al., Human Genetics 91:403–404 (1993).

| Allele | Frequency | Size (bp) | Number of repeats |
|--------|-----------|-----------|-------------------|
| A1 | 0.736 | 410 | 4 |
| A2 | 0.214 | 240 | 2 |
| A3 | 0.036 | 500 | 5 |
| A4 | 0.007 | 325 | 3 |
| A5 | 0.007 | 595 | 6 |

While investigators have observed a moderate association (Odds ratio ~2) between allele 2 of the VNTR polymorphism of IL-1ra and UC patients in Caucasian populations from North America and Europe, this association was too weak to be of diagnostic or prognostic value (allele 2 of IL-1ra present in 35% of UC versus 24% of controls). See, Mansfield, J. et al., Gastroenterology 106:637–642 (1994).

For the first time, it has been discovered that allele 2 of the VNTR polymorphism at intron 2 of IL-1ra can be used as a diagnostic and prognostic genetic marker of UC in humans of Jewish ancestry. Jewish UC patients have a significantly increased frequency of allele 2 compared with Jewish controls (Odds ratio=5), while non-Jewish UC patients have a frequency of allele 2 similar to non-Jewish controls.

More specifically, when the genotype at the IL-1ra locus was determined for unrelated Jewish and non-Jewish Caucasian human subjects with UC (n=106), CD (n=158), and controls (n=114) by PCR using the primers and procedures described below in greater detail, it was determined that the frequency of individuals carrying the allele 2 was significantly increased in the UC compared with controls (p=0.04; OR=1.7; 95% CI=1.0–3.1). CD patients had a similar frequency as controls (p=0.66). However, when this population was divided into Jewish and non-Jewish groups, a significant difference was only observed in Jews (p=0.003; OR=5.0; 95%CI=1.5–17.5), but not in non-Jews (p=0.85) as reported in detail in Table 2. The OR of 5 is the highest reported in any population.

TABLE 2

| Ethnic Groups | UC N | % of 2 | CD N | % of 2 | Controls N | % of 2 |
|---|---|---|---|---|---|---|
| Total Caucasian | 106* | 58.5 | 158* | 47.5 | 114* | 44.7 |
| Jews | 39 | 76.9 | 68 | 48.5 | 25 | 40.0 |
| Non-Jews | 66 | 48.5 | 88 | 46.6 | 81 | 46.9 |

*unknown ethnicity for 1 UC, 2 CD, and 8 controls

The $\chi^2$ test was used for the statistical test. Both Odds Ratio (OR) and its 95% confidence interval (CI) were calculated to measure the strength of associations.

Thus, in accordance with the present invention, there is provided methods of screening for UC in a human subject of Jewish ancestry, comprising detecting the presence or absence of nucleic acid encoding allele 2 of VNTR polymorphism at intron 2 of the IL-1ra gene in said subject, wherein the presence of nucleic acid encoding allele 2 is indicative of UC.

Nucleic acid of a subject which is suitable for screening in accordance with the present invention may be derived from any nucleated cell sample, and preferably from peripheral mononuclear blood cells.

"A human subject of Jewish ancestry" or "a person of Jewish ancestry" refers to a person having had at least one biologically-related grandparent who is Jewish. Preferably, the human subject is Caucasian of Jewish ancestry. Even more preferably, the human subject is an Caucasian of Ashkenazi Jewish ancestry.

Detecting the presence or absence of nucleic acid encoding allele 2 of the VNTR polymorphism of the IL-1ra gene may be accomplished by determining whether or not genomic DNA a the human subject possesses a defining characteristic of nucleic acid encoding allele 2 of the VNTR polymorphism of the IL-1ra gene. One of skill in the art will understand that there are many means available to make such a determination, e.g., electrophoresis, automated sequencing, allele-specific oligonucleotide probing, differential restriction endonuclease digestion, ligase-mediated gene detection, and the like.

For example, genomic DNA encoding at least intron 2 of the IL-1ra human gene can be isolated from nucleated cells of a human subject of Jewish ancestry and assayed for such characteristics as size, specific sequence, number of sequence repeats, ability to hybridize with a labeled probe under specific hybridization parameters, ability to bind with an antibody specific for a particular allele and the like, and then compared to a positive control which defines the same characteristic for allele 2 of the VNTR polymorphism and/or a negative control which defines the same characteristic for an allele of the VNTR polymorphism not known to be associated with UC in persons of Jewish ancestry.

A positive control for allele 2 of the VNTR polymorphism of the IL-1ra gene using the primers described herein for PCR amplification of genomic DNA and fragment length as the defining characteristic, a fragment of 240 base pairs would be a positive control and a negative control would be a fragments of 325, 410, 500 and/or 595 base pairs. Of course, the greatest likelihood of accurately detecting the presence of allele 2 of the VNTR polymorphism of the IL-1ra gene in this example would be to compare the results of the assay to the positive and negative control.

To increase the accuracy of detecting allele 2 of the VNTR polymorphism, the control should be subjected to the same test procedures and parameters as the nucleic acid of the subject being assayed. Likewise, assays to detect the presence or absence of nucleic acid encoding allele 2 of the VNTR polymorphism should be calibrated against a standard. For example, in a presently preferred embodiment using fragment length as the defining characteristic of alleles of the VNTR polymorphism, a positive control (a nucleic acid sequence known to encode allele 2 of the VNTR polymorphism) is amplified and electrophoresed using the same reagents, primers and parameters as that used for the nucleic acid of the subject being tested. A sequencing marker equal in size to the control is also subjected to electrophoresis using the same reagents and parameters as those used with the test and control nucleic acid. Sequencing markers useful in the practice of the present invention are available from a variety of commercial sources.

Genomic DNA of a subject encoding the sequence of interest at intron 2 of the IL-1ra gene can be amplified to make detection of the VNTR allele easier. Amplification of nucleic acid may be achieved using conventional methods, see, e.g., Maniatis, et al., Molecular Cloning: A Laboratory Manual 187–210 (Cold Spring Harbour Laboratory, 1982) which is incorporated herein by reference. Amplification, however, is preferably accomplished via the polymerase chain reaction ("PCR") method disclosed by U.S. Pat. Nos. 4,698,195 and 4,800,159, the respective contents of which are incorporated herein by reference. Application of PCR to detect alleles of the VNTR polymorphism of IL-1ra gene requires less DNA and is faster than standard Southern blotting and hybridization techniques.

Thus, oligonucleotide primer pairs can be constructed that allow enzymatic amplification of a subject's nucleic acid that encodes the VNTR polymorphism at intron 2 of the IL-1ra gene. The amplified nucleic acid can then be assayed to detect the presence or absence of allele 2.

Primer pairs suitable for use in the practice of the present invention are linear oligonucleotides ranging in length from about ten to about thirty nucleotides in length. One of the primers in the pair should be complementary to a nucleotide sequence upstream of the nucleic acid encoding the VNTR polymorphism at intron 2 of the IL-1ra gene targeted for amplification. The other primer should be complementary to a sequence located down stream of this target site. Preferably, the primers suitable for use in the present invention are specific for amplification of nucleic acid encoding VNTR polymorphism at intron 2 of the IL-1ra gene and do not prime amplification of nucleic acid which does not encode VNTR polymorphism of the IL-1ra gene. The sequences complementary to the primer pairs may be separated by as many nucleotides as the PCR technique and the other technique(s) for detecting the presence or absence of VNTR polymorphism will allow, provided that an appropriate control is used.

Primers suitable for use in amplifying genomic DNA encoding the VNTR polymorphism at intron 2 of the IL-1ra gene can be constructed using the oligonucleotide primer sequences described herein as well as the genomic sequence of the IL-1ra gene provided at Lennard, A. et al., Cytokine 4:83–89 (1992) and incorporated herein by reference.

A pair of primers suitable for use in the practice of the present invention is set forth in SEQ ID NOS 1 and 2. These primers are suitable for use in amplifying genomic DNA encoding the alleles of the VNTR polymorphism of intron 2 of the IL-1ra gene, and may be used as a pair or each in combination with another suitable primer.

The novel methods for screening for UC and for distinguishing UC from CD disclosed herein include the use of traditional diagnostic tests for UC in combination with the detection of nucleic acid of a subject encoding allele 2 of the VNTR polymorphism of IL-1ra. Thus, for example, a positive test for HLA DR2 and/or a positive pANCA status may be used in combination with detecting the presence of nucleic acid encoding allele 2 of the VNTR polymorphism.

Kits for use in screening for UC in human subjects of Jewish ancestry are also provided by the present invention. Such kits can include all or some of the positive controls, negative controls, reagents, primers, sequencing markers, probes and antibodies described herein for determining the presence or absence of nucleic acid encoding allele 2 of the VNTR polymorphism of the IL-1ra gene. Kits of the present invention may contain, for example, nucleic acid encoding allele 2 and/or alleles 1,3,4 and 5 of the VNTR polymorphism of the IL-1ra gene, the nucleic acid sequence of any one or more of these alleles, schedules of the number and type of nucleotide sequence repeats and characteristics of one or more of these alleles, one or more labeled oligonucleotide probes specific for one or more alleles of the VNTR alleles, one or more primers for amplification of nucleic acid encoding the VNTR polymorphism at intron 2 of the IL-1ra gene, reagents commonly used for amplification, polymerase, antibody specific for, or which binds particular VNTR alleles and combinations of any of the above.

As amenable, these suggested kit components may be packaged in a manner customary for use by those of skill in the art. For example, these suggested kit components may be provided in solution or as a liquid dispersion or the like.

A presently preferred embodiment of the inventive kits for use in screening for UC comprises DNA encoding allele 2 of the VNTR polymorphism of the IL-1ra gene in Tris-EDTA buffer solution preferably kept at 4° C.

Another embodiment of the inventive kits for use in screening for UC further comprises one or more primers specific for amplification of nucleic acid encoding the VNTR polymorphism at intron 2 of the IL-1ra gene, for example, primers selected from the group comprising SEQ ID NO 1 and SEQ ID NO 2.

Yet another embodiment of the inventive kits for use in screening for UC further comprises sequencing markers ranging in size from about 100 to about 600 base pairs.

EXAMPLES

Blood samples were obtained from 106 human patients diagnosed as having ulcerative colitis ("UC"), 158 human patients diagnosed as having Crohn's disease ("CD"), and 114 healthy humans ("controls"). The control group was selected to be ethnically and socioeconomically matched to the UC and CD patients. An individual was used as control only if he/she did not have inflammatory bowel disease, multiple sclerosis, systemic lupus erythematosus, or other recognized autoimmune diseases. The distribution of age, gender, and ethnicity (Jewish/non-Jewish) were comparable between patients and controls. A patient was considered to be Jewish if he/she was of Jewish ancestry, i.e., at least one of the patient's biological grandparents was Jewish. All patients and controls analyzed were Caucasians.

A. Isolation of Genomic DNA

Genomic DNA is isolated from blood samples of each patient and each of the control group by methods well known in the art, for example, by methods described in J. Sambrook, et al., Molecular Cloning: A Laboratory Manual, 2nd Edition, Cold Spring Harbor Laboratory Press (1989), incorporated herein by reference.

B. Amplification Of DNA Encoding Intron 2 of the IL-1ra Gene By PCR

The polymerase chain reaction ("PCR") was performed to amplify genomic DNA encoding intron 2 of the IL-1ra gene. The primers identified as SEQ ID NOs. 1 and 2 were used. The PCR reaction is performed in a total volume of 2 $\mu$l using 10 mM Tris-HCl (pH 8.3), 50 mM KCl, 1.5 mM $MgCl_2$, 0.15 $\mu$M primers, 200 $\mu$M each dATP, dCTP, dGTP, dTTP; 100 to 300 ng genomic, and two units Taq DNA polymerase.

PCR conditions are as follows: Denaturing of the nucleic acid sample in the first cycle of amplification is at 96° C. for one minute, followed by annealing primers at 60° C. for one minute, and polymerization at 70° C. for two minutes. Twenty nine subsequent cycles of amplification were carried out, denaturing at 94° C. for one minute, followed by annealing primers at 60° C. for one minute, and polymerization at 70° C. for two minutes. After the final round of amplification, the final PCR products are analyzed on a 2% agarose gel.

C. Electrophoresis of Amplified Genomic DNA Encoding Intron 2 of the IL-1ra Gene 20 $\mu$l amplified DNA is electrophoresed on a 2% agarose gel and stained with ethidium bromide. Gels are run with a 100 base pair ladder control DNA sequencing marker to size fragments. Although extra fragments may shadow the specific DNA bands, results are unambiguously interpretable, and confirmed by comparison to nucleic acid derived from human patients known to encode the specified alleles at Intron 2 of the IL-1ra gene and subjected to the same amplification and electrophoresis procedures described above.

Although the invention has been described with reference to presently preferred embodiments, it should be understood that various modifications can be made without departing from the spirit of the invention.

We claim:

1. A method of diagnosing a predisposition to ulcerative colitis in a human of Jewish ancestry, comprising obtaining from a human a biological sample comprising nucleated cells;

assessing the presence in the sample of a polynucleotide comprising at least a segment of allele 2 of the variable number of tandem repeats (VNTR) polymorphism at intron 2 of the human interleukin-1 receptor antagonist (IL-1ra) gene; and determining whether the human is of Jewish ancestry; and diagnosing a predisposition to ulcerative colitis (UC) when both the allele 2 polynucleotide, or fragments thereof, is detected and the human is of Jewish ancestry.

2. The method of claim 1, wherein the presence of the allele 2 polynucleotide is assessed by measuring the length of the polynucleotide, and comparing it to a control selected from the group consisting of positive and negative controls.

3. The method of claim 1, wherein the presence of the allele 2 polynucleotide is assessed by determining the sequence of the polynucleotide, and comparing it to a control selected from the group consisting of positive and negative controls.

4. The method of claim 1, wherein the presence of the allele 2 polynucleotide is assessed by determining whether a DNA of the human subject possesses a defining characteristics of allele 2 selected from the group consisting of size, specific sequence, number of sequence repeats, ability to hybridize with a labeled probe under specific hybridization conditions, and ability to bind with an antibody specific for a particular allele, wherein these characteristics are compared to a positive control which defines the same or similar characteristic for allele 2 of the VNTR polymorphism and/or a negative control with defines the same or similar characteristic for an allele of the VNTR polymorphism not known to be associated with UC in a person of Jewish ancestry.

5. The method of claim 3, wherein the presence of the allele 2 polynucleotide is assessed by determining the number of sequence repeats in the polynucleotide, and comparing it to a control selected from the group consisting of positive and negative controls.

6. The method of claim 1, wherein the nucleated cells in the sample comprise mononuclear blood cells.

7. The method of claim 1, wherein the ancestry of the human is determined as Jewish when at least one biologically-related grandparent of the human is of Jewish ancestry.

8. The method of claim 1, further comprising determining whether the human of Jewish ancestry is of Caucasian ancestry.

9. The method of claim 8, further comprising determining whether the human of Caucasian ancestry is of Ashkenazi ancestry.

10. The method of claim 1, wherein the allele 2 polynucleotide is detected by allele-specific nucleotide probing, and compared to a control selected from the group consisting of positive and negative controls.

11. The method of claim 1, wherein the allele 2 polynucleotide is detected by methods selected from the group consisting of differential restriction endonuclease digestion, electrophoresis, automated sequencing, allele-specific probing, and ligase-mediated gene detection and compared to a control selected from the group consisting of positive and negative controls.

12. The method of claim 2, wherein
the length of the allele 2 polypeptide is detected; and
the polynucleotide control is selected from the group consisting of a 240 nucleotides long positive control, and 325, 410, 500 and 595 nucleotides long negative controls.

13. The method of claim 1, wherein the polynucleotide is detected by
amplifying cellular genomic DNA; and
identifying the allele 2 polynucleotide of the VNTR polymorphism of the human IL-1ra gene.

14. The method of claim 13, wherein the amplifying step is conducted with primers specific for a polynucleotide encoding allele 2 of the VNTR polymorphism of the human IL-1ra gene.

15. The method of claim 14, wherein at least one primer is selected from the group consisting of SEQ ID NO 1, SEQ ID NO 2, and fragments thereof.

16. The method of claim 1, wherein the polynucleotide is detected by
sequencing the polynucleotide encoding a fragment of intron 2 of the VNTR allele of the IL-1ra gene; and
identifying the allele present by comparison to a control.

17. A method of determining whether an inflammatory bowel disease (IBD) patient of Jewish ancestry has ulcerative colitis, comprising
the method of claim 1, wherein the biological sample is obtained from a patient afflicted with IBD.

18. A method of distinguishing whether a human of Jewish ancestry has a predisposition to ulcerative colitis or Crohn's disease, comprising
obtaining from a human a biological sample comprising nucleated cells;
assessing the presence in the sample of a polynucleotide comprising at least a segment of allele 2 of the variable number of tandem repeats (VNTR) polymorphism at the interleukin-1 receptor antagonist (IL-1ra) gene;
determining whether the human is of Jewish ancestry; and
diagnosing a predisposition to ulcerative colitis when both the allele 2 polynucleotide is detected and the human is of Jewish ancestry.

19. A kit for diagnosing a predisposition to UC in humans of Jewish ancestry, comprising
at least one primer specific to a polynucleotide comprising a segment of intron 2 of allele 2 of the variable number of tandem repeats (VNTR) polymorphism at the interleukin-1 receptor antagonist (IL-1ra) gene; and
instructions for its use with nucleic acids of humans of Jewish ancestry.

20. The kit of claim 19, wherein the primers are about 10 to about 30 nucleotide long.

21. The kit of claim 19, wherein at least one of the primers is complementary to a nucleotide segment up-stream from the segment encoding the VNTR polymorphism.

22. The kit of claim 19, wherein at least one of the primers is complementary to a nucleotide segment down-stream from the segment encoding the VNTR polymorphism.

23. The kit of claim 19, wherein the polynucleotide comprises a segment of intron 2.

24. The kit of claim 23, wherein the polynucleotide comprises intron 2.

25. The kit of claim 19, in packaged form.

26. The kit of claim 19, further comprising an agent selected from the group consisting of
DNA markers;
DNA selected from the group consisting of primers and probes to, and DNA segments of, intron 2 of allele 1, 3, 4, and 5 of the IL-1ra gene encoding the VNTR polymorphism;
a control selected from the group consisting of positive and negative controls for allele 2 of the IL-1ra gene fragment encoding the VNTR polymorphism; and
DNA polymerizing enzyme(s).

27. The kit of claim 26, wherein the DNA markers comprise markers about 100 to about 600 nucleotides long.

28. The kit of claim 26, wherein the positive control comprises allele 2 of the IL-1ra gene fragment encoding the VNTR polymorphism.

29. The kit of claim 27, wherein the negative control comprises a DNA fragment selected form the group consisting of DNA fragments of allele 1, allele 3, allele 4, and allele 5 of the IL-1ra gene fragment encoding the VNTR polymorphism.

30. The kit of claim 19, wherein the primers are nucleic acids specified by SEQ. ID. NO.: 1 and/or SEQ. ID. NO.:2.

31. The method of claim 1, further comprising the step of using a standard diagnostic test for ulcerative colitis, wherein ulcerative colitis is thereby distinguished from Crohn's disease.

* * * * *

UNITED STATES PATENT AND TRADEMARK OFFICE
CERTIFICATE OF CORRECTION

PATENT NO. : 5,942,390
DATED : August 24, 1999
INVENTOR(S) : Fabio Cominelli, et al.

It is certified that error appears in the above-identified patent and that said Letters Patent is hereby corrected as shown below:

On the title page, item [73]:

After Cedars-Sinai Medical Center, Los Angeles, CA, please add as an assignee "University of Virginia Patent Foundation, Charlottesville, VA"

Signed and Sealed this

Eighth Day of August, 2000

*Attest:*

Q. TODD DICKINSON

*Attesting Officer*   *Director of Patents and Trademarks*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:1:

CTCAGCAACA CTCCTAT                                                    17

(2) INFORMATION FOR SEQ ID NO:2:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:2:

TCCTGGTCTG CAGGTAA                                                    17